United States Patent [19]

DiTucci

[11] Patent Number: 5,674,510

[45] Date of Patent: Oct. 7, 1997

[54] HAIR TREATMENT SOLUTION AND METHOD OF USING SAME

[76] Inventor: Ida DiTucci, 5 Lake Ter., Woburn, Mass. 01801

[21] Appl. No.: 557,582

[22] Filed: Nov. 14, 1995

[51] Int. Cl.$^6$ ...................................................... H61K 7/06
[52] U.S. Cl. ........................... 424/401; 424/47; 424/70.1; 514/881; 514/887
[58] Field of Search ................................... 424/401, 70.1, 424/72, 47; 514/881, 887

[56] References Cited

U.S. PATENT DOCUMENTS

| | | |
|---|---|---|
| 4,933,177 | 6/1990 | Grollier . |
| 5,026,553 | 6/1991 | Swinney . |
| 5,130,142 | 7/1992 | Wong et al. . |
| 5,152,990 | 10/1992 | Miyauchi . |

OTHER PUBLICATIONS

The Merck Index, 11th Edition, Compound No. 6122, Minoxidil (1989).

*Primary Examiner*—Thurman K. Page
*Assistant Examiner*—D. Faulkner
*Attorney, Agent, or Firm*—Wolf, Greenfield & Sacks, P.C.

[57] ABSTRACT

A hair treatment solution capable of acting as a cosmetic, reducing alopecia, eliminating alopecia, increasing hair growth or any combination thereof is disclosed. The hair treatment solution comprises garlic powder, brewer's yeast, grapefruit juice, acetic acid and kelp. In one aspect, the invention includes a method of applying the hair treatment solution. Typically, the solution is applied directly to a treatment area.

17 Claims, No Drawings

HAIR TREATMENT SOLUTION AND METHOD OF USING SAME

CROSS-REFERENCE TO RELATED APPLICATION

This application is a related application under 35 U.S.C. §120 to U.S. Ser. No. 08/188,572 filed on Jan. 24, 1994, and entitled I.R.V. Hair Solution.

BACKGROUND OF THE INVENTION

1. Field of the Invention

The present invention generally relates to hair treatment solutions, and more specifically to such a solutions which are capable of acting as a cosmetic, reducing alopecia, eliminating alopecia, stimulating hair growth or any combination thereof as well as methods of using same.

2. Discussion of the Related Art

Due to society's tendency to attach a stigma to hair loss, there exists a substantial demand for a "cure" to baldness. In particular, the desire to maintain a full head hair has resulted in numerous hair growth studies. These studies have led to several results with respect to the growth of hair.

In particular, it is now known that there are two features of the hair follicle. These include the epithelia and the dermal papilla which is a specialized dermal compartment. The epithelia give rise to the eperdermal stem cells which lead to the outer root sheath. The outer root sheath leads to the matrix cell which gives rise to the inner root sheath and hair fiber. The size of the dermalpapilla is related to the size of the hair follicle. In turn, the size of the follicle is related to the size of the hair produced. For example, terminal hair follicles on the scalp of haired individuals contain large dermalpappila and produce long, thick hair. However, the velluss follicles commonly observed on a bald scalp are small and produce short, thin hair. These velluss follicles contain a small dermalpapilla. Similar relationships have been observed in animals having fur, and it is now believed that the specific factors which regulate the size of the dermalpapilla may ultimately regulate hair growth.

In mammals, the pilar cycle occurs in the following phases: (1) angen, the active phase during which the cells of the hair bulb divide rapidly and form the hair; (2) catagen, the phase during which mitotic activity is slowed and the follicle atrophies; and (3) telogen, the rest phase of the follicles during which the hair progressively separates and falls out. "Alopecia" as used herein refers to the abnormal or natural loss of hair. For example, alopecia may occur when the hair pilar cycle is disturbed, resulting in excessive hair lost due to a shortening in the angenic phase. Consequently, transmission to the telogenic phase occurs earlier and hair removal from the scalp is increased. Gradually, the increasing shorter and finer hairs convert to an unpigmented down (vellus) which can eventually lead to baldness.

Alopecia can be caused by a variety of factors including, but not limited to, mental stress, hormonal imbalances, chemotherapy and febrile conditions. Alopecia is also attributed to advancing age and a decrease in the mitotic activity of the hair follicle.

It remains a challenge in the art to provide a solution that is capable of reducing and/or eliminating alopecia without any detrimental side effects. It is a further challenge in the art to provide a solution that is capable of increasing hair growth or acting as a cosmetic without inducing negative side effects.

SUMMARY OF THE INVENTION

Accordingly, it is an object of the present invention to provide a hair treatment solution that is capable of reducing alopecia.

It is another object of the present invention to provide a hair treatment solution that is capable of eliminating alopecia.

It is yet another object of the present invention to provide a hair treatment solution that provides increased hair growth.

It is still another object of the present invention to provide a hair treatment solution that, subsequent to ending its use, is capable of providing continued reduction of alopecia, elimination of alopecia, increased hair growth or any combination thereof.

It is a further object of the present invention to provide a hair treatment solution that is relatively easy to make.

It is still a further object of the present invention to provide a hair treatment solution that comprises comparatively readily available materials.

It is an object of the present invention to provide a method of using a hair treatment solution.

It is another object of the present invention to provide a hair treatment solution which is a cosmetic.

It is yet another object of the present invention to provide a hair treatment solution which does not have any negative side effects.

It is still a further object of the present invention to provide a hair treatment solution which is capable of stretching the skin and/or opening the pores of a treatment area.

In one embodiment, the present invention comprises a hair treatment solution which includes garlic powder, brewer's yeast, grapefruit juice, acetic acid and kelp. Each ingredient is present in an amount so that the solution is capable of acting as a cosmetic, reducing alopecia, eliminating alopecia, increasing hair growth or any combination thereof.

In another embodiment, the present invention comprises a method of applying a hair treatment solution which includes placing the hair treatment solution in contact with a treatment area. The application of the solution should reduce alopecia, eliminate alopecia, increase hair growth, allow the solution to act as a cosmetic or any combination thereof.

DETAILED DESCRIPTION

The present invention relates to a hair treatment solution. In certain embodiments, the hair treatment solution should not yield any negative side effects. The solution is capable of acting as a cosmetic, reducing alopecia, eliminating alopecia, increasing hair growth or any combination thereof. The solution comprises garlic powder, brewer's yeast, grapefruit juice, acetic acid and kelp. In a particularly preferred embodiment, the hair treatment solution comprises, by weight, about 82% garlic powder, about 8% brewer's yeast, about 5% grapefruit juice, about 2% acetic acid and about 3% kelp. In this embodiment, the garlic powder, brewer's yeast and kelp are supplied by aged garlic pills.

"Negative side effects" as used herein refer to side effects which are harmful or undesirable to the subject of the treatment. Such side effects include, but are not limited to, a dry scalp, a burning scalp, or a rash.

A "cosmetic" as used herein denotes a composition of matter which can provide improved qualities to skin. Such qualities include, for example, cleansing of the treatment area.

"Treatment area" herein denotes an area to which the hair treatment solution is applied. Such an area typically includes an at least partially bald human head.

By "reduced alopecia" it is herein meant to refer to a noticeable decrease in hair loss over a period of several weeks.

"Eliminated alopecia" herein denotes no noticeable hair loss over several weeks.

"Increased hair growth" refers to a visually discernable increase in hair growth over several weeks. Typically, such increased hair growth occurs with very fine, white hairs and eventually proceeds to thicker, colored hair.

By "solution" it is herein meant to refer to a composition of matter which may or may not be in a liquid state. Thus, solutions include gases, liquids and solids. Preferably, the hair treatment solution is a liquid.

Any amount of garlic powder may be-included within the hair solution so long as the solution is capable of acting as a cosmetic, reducing alopecia, eliminating alopecia, increasing hair growth or any combination thereof. Preferably, the hair treatment solution comprises, by weight, from about 67% to about 97% garlic powder, more preferably from about 72% to about 92% garlic powder and most preferably about 82% garlic powder. It should be noted that as the relative amount of garlic powder is increased, the effectiveness of the hair treatment solution does not increase. However, as the relative amount of garlic powder is decreased, the effectiveness of the solution decreases. Typically, the garlic powder is provided in the form of pills.

Preferably, the hair treatment solution comprises, by weight, from about 2% to about 14% brewer's yeast, more preferably from about 5% to about 11% brewer's yeast and most preferably about 8% brewer's yeast. While certain ranges of brewer's yeast have been disclosed herein, it is to be appreciated that the amount of brewer's yeast is limited only in that the hair treatment solution should be capable of acting as a cosmetic, reducing alopecia, eliminating alopecia, increasing hair growth or any combination thereof. Typically, the brewer's yeast is supplied in the form of a pill along with the garlic powder.

The hair treatment solution may include any amount of grapefruit juice so long as the solution acts as a cosmetic, reduces alopecia, eliminates alopecia, increases hair growth or any combination thereof. Preferably, the hair treatment solution comprises, by weight, no more than about 7% grapefruit juice, more preferably no more than about 6% grapefruit juice and most preferably about 5% grapefruit juice. It is to be understood that other sources of citric acid may also be used so long as they provide the hair treatment solution has the desired properties. For example, lemon juice may be used instead of grapefruit juice.

The amount of acetic acid used within the hair treatment solution of the present invention may be varied anywhere within a range that allows the hair treatment solution to provide reduced alopecia, eliminated alopecia, increased hair growth, act as a cosmetic or any combination thereof. Preferably, the hair treatment solution comprises, by weight, no more than about 4% acetic acid, more preferably no more than about 3% acetic acid and most preferably about 2% acetic acid. Any form of acetic acid may be used so long as the hair treatment solution has the desired properties. Preferably, the acetic acid is red cider vinegar.

Preferably, the hair treatment solution comprises, by weight, at most about 5% kelp, more preferably at most about 4% kelp and most preferably about 3% kelp. However, it is to be understood that the hair treatment solution may include other ranges of kelp so long as the solution is capable of acting as a cosmetic, reducing alopecia, eliminating alopecia, increasing hair growth or any combination thereof. The kelp may be supplied by any source. Typically, the kelp is provided in the form of a pill along with the garlic powder.

The hair treatment solution of the present invention is designed to provide reduced alopecia, eliminated alopecia, increased hair growth, act as a cosmetic or any combination thereof. Ideally, hair growth is optimized and alopecia is minimized by the hair treatment solution. Methods of testing various combinations of the components of the hair treatment solution of the present invention for effectiveness would be obvious to those skilled in the art. For example, one simple test for determining an appropriate combination of ingredients would be as follows. Several solutions comprising different amounts of the components are made according to methods disclosed herein. An amount of each solution is applied to a bald human scalp, and any change in hair loss or increase in hair growth is monitored for a given period of time.

Methods of applying the hair treatment solution are limited only in that the solution should be allowed to reduce alopecia, eliminate alopecia, increase hair growth, act as a cosmetic or any combination thereof. Typically, the solution is applied directly to the treatment area. For example, the solution may be brushed onto the treatment area. Alternatively, a pharmaceutically acceptable carrier may be used during application of the solution. Such carriers are known to those skilled in the art.

It is believed that optimal results are achieved when at least about ½ ounce of the hair treatment solution is applied directly to the treatment area for at least about three hours. Such treatment should be carried out at least twice a week for at least about two months. While certain treatment conditions have been disclosed herein, it is to be understood that other treatment conditions may also provide the desired properties of the present invention.

Treatment of an area of skin with the hair treatment solution usually results in concentric growth of hair. By "concentric growth of hair" it is herein meant to refer to hair growth which grows substantially radially from a center point.

It has been found that in certain embodiments the hair treatment solution is capable of stretching the skin and/or opening the pores of a subject's treatment area. It is believed that this may, at least in part, explain the ability of the solution of the present invention to provide its desirable properties.

The following examples demonstrate the effectiveness of the hair treatment solution of the present in enhancing hair growth.

EXAMPLE 1

A hair treatment solution comprising 82.2% by weight garlic powder, 8.2% by weight brewer's yeast, 4.6% by weight grapefruit juice, 2.3% by weight acetic acid (5% aqueous) and 2.7% by weight kelp was prepared by combining the ingredients in a glass container at room temperature. The garlic powder, brewer's yeast and kelp were provided in the form of Kyolic aged garlic pills (manufactured by Wakanuga of America Company located in Mission Viejo, Calif., 92961). The ingredients were then stirred thoroughly to create a viscous, brown-colored liquid. The solution was applied to the bald scalp of a 80 year old male. The subject had been bald for about 50 years.

About ½ ounce of the solution was applied to the subject's scalp at a frequency of three applications per week. During each treatment, the solution was kept on the subject's scalp for at least about three hours before being removed therefrom. After approximately three weeks, reduced and eliminated alopecia were observed. In addition, after about three weeks, increased hair growth was noticed.

EXAMPLE 2

A hair treatment solution as in Example was applied to a bald scalp of a 65 year old adult male who had been bald for about 20 years. During each treatment, about ½ ounce of the solution was applied to the treatment area, and the solution was kept on the scalp for at least about three hours. Such treatments were repeated at a frequency of about three applications per week. After a period of about three weeks, alopecia was reduced and eliminated after about three weeks. Furthermore, increased hair growth was noticed after about three weeks.

EXAMPLE 3

A hair treatment solution as in Example 1 was applied to the bald scalp of a 40 year old adult male who had been bald for about ten years. During each treatment, about ½ ounce of the solution were applied to the treatment area, and the solution was kept on the treatment area for at least about three hours. Such treatments were carried out at a frequency of about three applications per week. After a period of about three weeks, reduced alopecia was observed. Alopecia was eliminated after about three weeks. Increased hair growth was noticed after about rotor weeks.

Having thus described certain embodiments of the invention, various alterations, modifications and improvements will readily occur to those skilled in the art. Such alterations, modifications and improvements are intended to be part of this disclosure, and are intended to be within the spirit and scope of the invention. Accordingly, the foregoing description is by way of example only and is not intended as limiting. The invention is limited only as defined in the following claims and the equivalents thereto.

What is claimed is:

1. A hair treatment solution comprising:
   garlic powder;
   brewer's yeast;
   grapefruit juice;
   acetic acid; and
   kelp, wherein the hair treatment solution is formulated to reduce alopecia.

2. The hair treatment solution according to claim 1, wherein the hair treatment solution comprises, by weight, from about 67% to about 97% garlic powder.

3. The hair treatment solution according to claim 1, wherein the hair treatment solution comprises, by weight, from about 2% to about 14% brewer's yeast.

4. The hair treatment solution according to claim 1, wherein the hair treatment solution comprises, by weight, at most about 7% grapefruit juice.

5. The hair treatment solution according to claim 1, wherein the hair treatment solution comprises, by weight, at most about 4% acetic acid.

6. The hair treatment solution according to claim 1, wherein the hair treatment solution comprises, by weight, at most about 5% kelp.

7. The hair treatment solution according to claim 1, wherein the hair treatment solution comprises, by weight, about 82% garlic powder, about 8% brewer's yeast, about 5% grapefruit juice, about 2% acetic acid and about 3% kelp.

8. A hair treatment solution comprising:
   garlic powder;
   brewer's yeast;
   grapefruit juice;
   acetic acid; and
   kelp, wherein the hair treatment solution is formulated to eliminate alopecia.

9. The hair treatment solution according to claim 8, wherein the hair treatment solution comprises, by weight, about 82% garlic powder, about 8% brewer's yeast, about 5% grapefruit juice, about 2% acetic acid and about 3% kelp.

10. A hair treatment solution comprising:
    garlic powder;
    brewer's yeast;
    grapefruit juice;
    acetic acid; and
    kelp, wherein the hair treatment solution is formulated to increase hair growth.

11. The hair treatment solution according to claim 10, wherein the hair treatment solution comprises, by weight, about 82% garlic powder, about 8% brewer's yeast, about 5% grapefruit juice, about 2% acetic acid and about 3% kelp.

12. A method of applying a hair treatment solution, the method comprising the step of:
    contacting the hair treatment solution with an a treatment area so that alopecia is reduced, wherein the hair treatment solution includes garlic powder, brewer's yeast, grapefruit juice, acetic acid and kelp.

13. The method according to claim 12, wherein the contacting step includes applying the hair treatment solution topically.

14. The method of applying a hair treatment solution according to claim 12, wherein the contacting step includes applying the hair treatment solution in discrete treatments, each discrete treatment including an application of at least about ½ ounce of the hair treatment solution to the treatment area.

15. The method according to claim 12, wherein the contacting step includes applying the hair treatment solution in discrete treatments, each discrete treatment having an application time to the treatment area of at least about three hours.

16. The method according to claim 12, wherein the contacting step includes brushing the hair treatment solution onto the treatment area.

17. The method according to claim 12, wherein the contacting step includes applying the hair treatment solution in discrete treatments, the discrete treatments having a frequency of at least two times a week.

* * * * *